United States Patent
McNamara et al.

(10) Patent No.: US 12,329,532 B2
(45) Date of Patent: Jun. 17, 2025

(54) APPARATUS AND METHOD FOR PHASE TRACKING AN OSCILLATORY SIGNAL

(71) Applicant: Oxford University Innovation Limited, Oxford (GB)

(72) Inventors: Colin Gerard McNamara, Oxford (GB); Andrew David Sharott, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 951 days.

(21) Appl. No.: 17/437,869

(22) PCT Filed: Mar. 10, 2020

(86) PCT No.: PCT/GB2020/050576
§ 371 (c)(1),
(2) Date: Sep. 10, 2021

(87) PCT Pub. No.: WO2020/183152
PCT Pub. Date: Sep. 17, 2020

(65) Prior Publication Data
US 2022/0183612 A1 Jun. 16, 2022

(30) Foreign Application Priority Data
Mar. 12, 2019 (GB) .................................... 1903363

(51) Int. Cl.
*A61B 5/374* (2021.01)
*A61B 5/397* (2021.01)
(Continued)

(52) U.S. Cl.
CPC .............. *A61B 5/374* (2021.01); *A61B 5/397* (2021.01); *A61N 1/0529* (2013.01);
(Continued)

(58) Field of Classification Search
CPC ...... A61B 5/374; A61B 5/397; A61N 1/0529; A61N 1/36139; G06F 1/0335; G01R 23/12; G01R 23/18
See application file for complete search history.

(56) References Cited

U.S. PATENT DOCUMENTS 6,396,889 B1   5/2002  Sunter et al.
6,483,361 B1   11/2002 Chiu
(Continued)

FOREIGN PATENT DOCUMENTS

WO    2006/024102 A1   3/2006
WO    2016/028635 A1   2/2016
(Continued)

OTHER PUBLICATIONS

International Search Report and Written Opinion for WO 2020/183152 (PCT/GB2020/050576), dated Aug. 26, 2020, pp. 1-20.
(Continued)

*Primary Examiner* — Christopher A Flory
(74) *Attorney, Agent, or Firm* — Thomas|Horstemeyer, LLP

(57) ABSTRACT

Apparatus and methods for phase tracking an oscillatory signal are provided. In one arrangement, an input signal is received. First and second reference oscillatory signals are received at the frequency of a target frequency component of the input signal. The first and second reference oscillatory signals are phase shifted relative to each other. Weights of a weighted sum of the first and second reference oscillatory signals are iteratively varied to match the weighted sum to the input signal. The weights of the matched weighted sum are used to provide real time estimates of the phase of the target frequency component of the input signal.

22 Claims, 10 Drawing Sheets

(51) Int. Cl.
    *A61N 1/05*         (2006.01)
    *A61N 1/36*         (2006.01)
    *G01R 23/12*        (2006.01)
    *G01R 23/18*        (2006.01)
    *G06F 1/03*         (2006.01)

(52) U.S. Cl.
    CPC ....... *A61N 1/36139* (2013.01); *G06F 1/0335* (2013.01); *G01R 23/12* (2013.01); *G01R 23/18* (2013.01)

(56) References Cited

U.S. PATENT DOCUMENTS

| | | | | |
|---|---|---|---|---|
| 7,209,787 | B2* | 4/2007 | DiLorenzo | A61N 1/36082 607/45 |
| 7,231,254 | B2* | 6/2007 | DiLorenzo | A61N 1/3605 607/45 |
| 7,623,928 | B2* | 11/2009 | DiLorenzo | A61N 1/36064 607/45 |
| 9,042,988 | B2* | 5/2015 | DiLorenzo | A61N 1/3605 607/45 |
| 9,295,838 | B2* | 3/2016 | Starr | A61N 1/0531 |
| 2007/0142862 | A1 | 6/2007 | Dilorenzo | |
| 2009/0076402 | A1 | 3/2009 | Hoium et al. | |
| 2014/0200822 | A1 | 7/2014 | Dubois et al. | |
| 2014/0257128 | A1* | 9/2014 | Moxon | A61B 5/6868 607/45 |
| 2016/0143594 | A1* | 5/2016 | Moorman | A61B 5/7246 705/2 |
| 2016/0147964 | A1* | 5/2016 | Corey | G16H 40/63 700/90 |
| 2016/0220836 | A1 | 8/2016 | Parks | |
| 2016/0317807 | A1 | 11/2016 | Ma et al. | |
| 2017/0128729 | A1* | 5/2017 | Netoff | A61N 1/36139 |
| 2018/0110991 | A1* | 4/2018 | Molnar | G16H 20/30 |
| 2018/0365194 | A1* | 12/2018 | Grado | G06F 17/147 |
| 2019/0307345 | A1* | 10/2019 | Weiss | A61B 5/24 |
| 2022/0183612 | A1* | 6/2022 | Mcnamara | A61N 1/36082 |

FOREIGN PATENT DOCUMENTS

| | | |
|---|---|---|
| WO | 2017/172728 A1 | 10/2017 |
| WO | 2019/018879 A1 | 1/2019 |

OTHER PUBLICATIONS

UK Search Report for GB 1903363.8, dated Aug. 20, 2019, pp. 1-4.
Cagnan et al. (2013). Phase dependent modulation of tremor amplitude in essential tremor through thalamic stimulation. Brain 136, 3062-3075.
Cordon et al. (2018). Theta-phase closed-loop stimulation induces motor paradoxical responses in the rat model of Parkinson disease. Brain Stimul 11, 231-238.
Siegle et al. (2014). Enhancement of encoding and retrieval functions through theta phase-specific manipulation of hippocampus. Elife 3, e03061.
Berenyi et al. (2012). Closed-loop control of epilepsy by transcranial electrical stimulation. Science 337, 735-737.
Chen et al. (2013). Real-time brain oscillation detection and phase-locked stimulation using autoregressive spectral estimation and time-series forward prediction. IEEE Trans Biomed Eng 60, 753-762.
Jackson et al. (2015). Computationally efficient, configurable, causal, real-time phase detection applied to local field potential oscillations. I Ieee EMBS C Neur E, 942-947.
Van Zaen et al. (2010). Adaptive tracking of EEG oscillations. J Neurosci Methods 186, 97-106.
Nicholson et al. (2018), Analog closed-loop optogenetic modulation of hippocampal pyramidal cells dissociates gamma frequency and amplitude, bioRxiv.
Zanos et al. (2018) Phase-Locked Stimulation during Cortical Beta Oscillations Produces Bidirectional Synaptic Plasticity in Awake Monkeys, Current Biology 28, 2515-2526.e2514.
Aviyente et al. (2010). A phase synchrony measure for quantifying dynamic functional integration in the brain, Human Brain Mapping, vol. 32, Issue 1, pp. 80-93.
Adhikari et al. (2016). A Quaternion Weighted Fourier Linear Combiner for Modeling Physiological Tremor, IEEE Transactions on Biomedical Engineering, vol. 63, No. 11, Nov. 2016.
Azodi Avval et al. (2015). Phase-dependent modulation as a novel approach for therapeutic brain stimulation, Front. Comput. Neurosci., Feb. 26, 2015.
Engel et al. (2001). Dynamic Predictions: Oscillations and Synchrony in Top-Down Processing, Nat Rev Neurosci 2, 704-716.
Holt et al. (2016). Phasic Burst Stimulation: A Closed-Loop Approach to Tuning Deep Brain Stimulation Parameters for Parkinson's Disease, PLoS Comput Biol 12(7).
Meidahl et al. (2017). Adaptive Deep Brain Stimulation for Movement Disorders: The Long Road to Clinical Therapy, Mov Disord. Jun. 2017;32(6):810-819.
Moll et al. (2017). Phase matters: cancelling pathological tremor by adaptive deep brain stimulation, Brain, vol. 140, Issue 1, Jan. 2017, pp. 5-8.
Schnitzler et al. (2005). Normal and Pathological Oscillatory Communication in the Brain, Nat Rev Neurosci 6, 285-296.
Vaz et al. (1989). Adaptive Fourier estimation of time-varying evoked potentials, IEEE Transactions on Biomedical Engineering, vol. 36, No. 4, pp. 448-455, Apr. 1989.
Vaz et al. (1994). An Adaptive Estimation of Periodic Signals Using a Fourier Linear Combiner, IEEE Transactions on Signal Processing, vol. 42, No. 1, pp. 1-10, Jan. 1994.
Veluvolu et al. (2007). Bandlimited Multiple Fourier Linear Combiner for Real-time Tremor Compensation, 29th Annual International Conference of the IEEE Engineering in Medicine and Biology Society, 2007, pp. 2847-2850.
Venkatraman et al. (2009). A System for Neural Recording and Closed-Loop Intracortical Microstimulation in Awake Rodents, IEEE Transactions on Biomedical Engineering, vol. 56, No. 1, pp. 15-22, Jan. 2009.
Volder (1959). The CORDIC Trigonometric Computing Technique, IRE Transactions on Electronic Computers, vol. EC-8, No. 3, pp. 330-334, Sep. 1959.
International Preliminary Report on Patentability for WO 2020/183152 (PCT/GB2020/050576), dated Aug. 25, 2021, pp. 1-13.

* cited by examiner

APPARATUS AND METHOD FOR PHASE TRACKING AN OSCILLATORY SIGNAL

CROSS-REFERENCE TO RELATED APPLICATIONS

This application is the National Stage of International Application No. PCT/GB2020/050576, filed Mar. 10, 2020, which claims priority to GB 1903363.8, filed Mar. 12, 2019, which are entirely incorporated herein by reference.

The invention relates to phase tracking signals in real-time, particularly in the context of signals representing measurements of activity in a biological system such as the human nervous system, and for using the phase tracking to apply phase locked stimulation.

Neural oscillations play a fundamental role in normal brain processing by temporally coordinating activity within and across regions. Dysfunctional communication resulting from an inability to properly modulate oscillatory activity, either through hypo- or hyper-synchrony, has been implicated in a number of neurological disorders. Real-time manipulations directly locked to these oscillations have the potential to be of therapeutic benefit by correcting aberrant brain activity.

Various brain oscillations between 4 and 300 Hz mediate communication between brain cells (neurons). In deep brain structures, activities can be measured using a local field potential (LFP), a wide-band recording capturing both action potentials and other membrane potential-derived fluctuations in a small neuronal volume, typically made using a microelectrode. An equivalent recording, the electrocorticogram (ECoG), can be recorded from the cortical surface or surface of the scull (electroencephalogram; EEG). Oscillatory activity can also be measured from the muscles (electromyography; EMG) and are prevalent in movement disorders. Furthermore, rhythmic and oscillatory activity can be measured using light sensors when cellular populations are made to express light emitting indicators which in turn are sensitive to different molecules, ions or membrane potentials. Specific frequencies in particular brain areas are associated with definable functions and in disease these oscillations can show abnormal properties in a manner specific to the disorder. Several neural oscillations in different brain areas and disease states occur below 15 Hz. In the healthy brain, these include the slow (around 1 Hz) and delta (1-4 Hz) oscillations that occur during sleep, theta oscillations (4-12 Hz) in circuits controlling navigation, and cortical alpha oscillations (8-12 Hz). A crucial feature of these lower frequency activities is that they show a high degree of stationarity, maintaining a stable phase, frequency and amplitude over timescales of seconds to 10 s of seconds. In contrast, beta band (15-35 Hz) oscillations in the motor system emerge from the noise floor as transient "bursts" of increased amplitude and increased occurrence of this correlates with symptom severity in Parkinson's Disease. Fluctuations in gamma band activity (40-90 Hz) in similarly transient bursts are associated with many brain functions and abnormalities associated with a wide range of disease states including schizophrenia. Ripples in the hippocampus are amongst the fastest (135-250 Hz) neuronal oscillations, lasting for 5-8 cycles and are associated with memory consolidation.

It is thought that an effective way to modulate and manipulate neural oscillations is to perturb neuronal oscillations at a specific phase. The accuracy and hence potentially efficacy of such a strategy depends on and can be enhanced by accurate tracking of the instantaneous phase of the ongoing oscillation in the LFP, ECoG, EEG, EMG or other indicator signal. In addition, any effective phase tracking system used in this way must still remain responsive and accurate when functioning in a "closed-loop," whereby any perturbation that is being applied can change various parameters (e.g. amplitude, phase, frequency) of the input signal. Many perturbations, particularly electrical stimulation, will also cause signal artefacts that can potentially disturb phase tracking.

Several studies have achieved phase-dependent perturbations of stable oscillations in the lower frequency range (15 Hz). Some of these studies have used combinations of commercially available recording equipment, with some custom modification, to perform a threshold crossing/peak detection operation on a filtered local field potential signal. Examples include the following:

Cagnan, H., Brittain, J. S., Little, S., Foltynie, T., Limousin, P., Zrinzo, L., Hariz, M., Joint, C., Fitzgerald, J., Green, A. L., et al. (2013). Phase dependent modulation of tremor amplitude in essential tremor through thalamic stimulation. Brain 136, 3062-3075;

Cordon, I., Nicolas, M. J., Arrieta, S., Alegre, M., Artieda, J., and Valencia, M. (2018). Theta-phase closed-loop stimulation induces motor paradoxical responses in the rat model of Parkinson disease. Brain Stimul 11, 231-238; and Siegle, J. H., and Wilson, M. A. (2014). Enhancement of encoding and retrieval functions through theta phase-specific manipulation of hippocampus. Elife 3, e03061.

Other studies have used the filtered signal to drive stimulation directly, for example as described in Berenyi, A., Belluscio, M., Mao, D., and Buzsaki, G. (2012). Closed-loop control of epilepsy by transcranial electrical stimulation. Science 337, 735-737.

The following publications conceptually design systems to track phase of stable, low frequency oscillations, but without describing circuit implementations:

Chen, L. L., Madhavan, R., Rapoport, B. I., and Anderson, W. S. (2013). Real-time brain oscillation detection and phase-locked stimulation using autoregressive spectral estimation and time-series forward prediction. IEEE Trans Biomed Eng 60, 753-762;

Jackson, J. C., Corey, R., Loxtercamp, G., Stanslaski, S., Orser, H., and Denison, T. (2015). Computationally efficient, configurable, causal, real-time phase detection applied to local field potential oscillations. I Ieee Embs C Neur E, 942-947; and Van Zaen, J., Uldry, L., Duchene, C., Prudat, Y., Meuli, R. A., Murray, M. M., and Vesin, J. M. (2010). Adaptive tracking of EEG oscillations. J Neurosci Methods 186, 97-106.

Even at low frequencies, however, without description of implementations it is unclear how the algorithms would cope with the real-time perturbations.

Considering the more challenging problem of dealing with higher frequencies, Nicholson, E., Kuzmin, D., Leite, M., Akam, T. E., and Kullmann, D. M. (2018), Analog closed-loop optogenetic modulation of hippocampal pyramidal cells dissociates gamma frequency and amplitude, bioRxiv discloses phase-dependent closed-loop optogenetic stimulation of gamma oscillations in brain slices. However, the gamma oscillations were externally driven by excitation of the slice and the stimulation was then driven using a simple function of the LFP and its time derivative. Importantly, the methods used in this study did not necessitate that the phase was derived from a transient signal with fluctuations in the band of interest that could be masked by other lower frequency activities, but rather the gamma oscillation was driven constantly (over seconds) to a level where the stable raw signal could be used for feedback.

Zanos, S., Rembado, I., Chen, D., and Fetz, E. E. (2018) Phase-Locked Stimulation during Cortical Beta Oscillations Produces Bidirectional Synaptic Plasticity in Awake Monkeys Current Biology 28, 2515-2526.e2514 disclosed a method providing phase selective stimulation for three consecutive cycles of beta oscillations during short periods of elevated beta power. This was achieved using a PC with software that monitored the signals and accordingly activated the stimulation. Signalling delays associated with such a system were compensated for by measuring the delays with calibration waves of different frequencies. For a given target phase and frequency, stimulation was triggered appropriately early to compensate for the input and calculation delays (e.g. to hit the peak, if the delay is about three quarters of a cycle, stimulation was triggered on the previous descending phase). This approach means that the data samples in the intervening period (duration equal to the delay) cannot be used in the calculation. This is not a problem for stable oscillations but comes at a cost to accuracy in situations where there is more fluctuation in the input signal. As many real world signals are constantly fluctuating (e.g. over 100 s of milliseconds in the case of ongoing higher frequency oscillations prevalent throughout the brain), a highly responsive system is desirable for driving closed-loop interventions informed by phase.

It is an object of the invention to at least partly address one or more of the issues described above.

According to an aspect, there is provided an apparatus for phase tracking an oscillatory signal, comprising: an input unit configured to receive an input signal; and a phase estimation unit, wherein the phase estimation unit is configured to: generate first and second reference oscillatory signals at the frequency of a target frequency component of the input signal, the first and second reference oscillatory signals being phase shifted relative to each other; iteratively vary weights of a weighted sum of the first and second reference oscillatory signals to match the weighted sum to the input signal; and use the weights of the matched weighted sum to provide real time estimates of the phase of the target frequency component of the input signal.

The apparatus as thus configured allows effective phase tracking of oscillations in real-time even where the oscillations are transient and at higher frequencies (e.g. above 30 Hz) in a configuration that can be implemented at low cost and without requiring high power electronics.

In an embodiment, the input signal represents measurements of activity in a biological system. A stimulation unit generates a stimulation signal for applying phase locked stimulation to the biological system based on the estimates of phase provided by the phase estimation unit. The stimulation unit triggers a time-localised stimulation in response to the estimated phase passing through a predetermined phase threshold or into a predetermined phase range. The stimulation unit suppresses triggering of the time-localized stimulation in a case where the estimated phase passes through the predetermined phase threshold or into the predetermined phase range within a time period shorter than a predetermined fraction of a period of the target frequency component since a preceding passing of the estimated phase through the predetermined phase threshold or into the predetermined phase range.

This approach ensures reliable control of stimulation timing even in the presence of significant fluctuation in the estimated phase of the input signal, without introducing significant additional processing load or power requirements.

In an embodiment, the phase estimation unit accesses values of the first reference oscillatory signal and the second reference oscillatory signal from a look-up table. The look-up table stores: a first reference value for each of a plurality of time points representing a sequence of points in time, the variation of first reference value as a function of time point defining the oscillatory form of the first reference oscillatory signal; and a second reference value for each of the plurality of time points, the variation of second reference value as a function of time point defining the oscillatory form of the second reference oscillatory signal. The phase estimation unit comprises circuitry configured to perform predetermined data processing operations during each of a plurality of clock cycles. The apparatus adaptively controls the frequency of the first and second reference oscillatory components. In an embodiment, the adaptive control is implemented by changing the duration of the clock cycle. Alternatively or additionally, the phase estimation unit comprises a plurality of the look-up tables, each look-up table having a different number of time points, and the adaptive control is implemented by selectively switching between different ones of the look-up tables.

This approach allows the apparatus to follow changes in frequency of signals of interest without introducing significant additional processing load or power requirements.

According to an alternative aspect, there is provided an apparatus for phase tracking an oscillatory signal, comprising: an input unit configured to receive an input signal; and a phase estimation unit configured to output data representing when an estimated phase of a target frequency component of the input signal passes through a predetermined phase threshold or into a predetermined phase range in each of at least a subset of cycles of the target frequency component of the input signal, wherein: the phase estimation unit is further configured to: determine, for each passing of the estimated phase through the predetermined phase threshold or into the predetermined phase range, whether the estimated phase has passed through the predetermined phase threshold or into the predetermined phase range within a time period shorter than a predetermined fraction of a period of the target frequency component since a preceding passing of the estimated phase through the predetermined phase threshold or into the predetermined phase range; and output data representing a result of the determination.

According to an alternative aspect, there is provided a method of phase tracking an oscillatory signal, comprising: receiving an input signal; generating first and second reference oscillatory signals at the frequency of a target frequency component of the input signal, the first and second reference oscillatory signals being phase shifted relative to each other; iteratively varying weights of a weighted sum of the first and second reference oscillatory signals to match the weighted sum to the input signal; and using the weights of the matched weighted sum to provide real time estimates of the phase of the target frequency component of the input signal.

According to alternative aspect, there is provided a method of phase tracking an oscillatory signal, comprising: receiving an input signal; determining when an estimated phase of a target frequency component of the input signal passes through a predetermined phase threshold or into a predetermined phase range in each of at least a subset of cycles of the target frequency component of the input signal; and determining, for each passing of the estimated phase through the predetermined phase threshold or into the predetermined phase range, whether the estimated phase has passed through the predetermined phase threshold or into the predetermined phase range within a time period shorter than a predetermined fraction of a period of the target frequency component since a preceding passing of the estimated phase through the predetermined phase threshold or into the predetermined phase range; and outputting data representing a result of the determination.

Embodiments of the invention will now be described, by way of example only, with reference to the accompanying drawings in which corresponding reference symbols indicate corresponding parts:

FIG. 1 schematically depicts an apparatus for phase tracking an oscillatory signal such as a neuronal signal;

FIG. 2 schematically depicts an example architecture for a phase estimation unit;

A number of different approaches to phase tracking in a frequency band of interest are possible. For instance, a pass band filter followed by a phase extraction step such as a Hilbert transform can be used. Many such approaches suffer from inherent time delays. This can be thought of as including future data in the estimate of phase at a given time point. This is not a problem in offline analysis but limits the utility of such approaches in real-time applications that require instant intervention. Another consideration for real-time embedded applications is computational complexity causing increased power consumption and potentially variable time lags caused by buffering, interrupts and pre-emptive scheduling associated with pipelined high throughput computing architectures. Related to this is the consideration of whether to perform a continuous transformation on the incoming data stream or alternatively operate on chunks of data performing the entire calculation across the window before stepping the window forward and repeating the operation with the arrival of new data samples.

Embodiments of the present disclosure, described in further detail below, provide a desirable trade-off between minimising the required computational power while maximising performance and suitability. The embodiments were developed using real recordings to refine the requirements and prevent the addition of unnecessary complexity in the approach. Because the approaches described operate as a continuous transform of an incoming wide band data stream requiring only a short calculation to be performed per incoming sample, it can be implemented as a digital circuit, run on the most basic digital signal processors or even on a simple embedded controller. Furthermore, in the examples described, only 36 bits or three registers of state information need to be retained.

Figure 1:
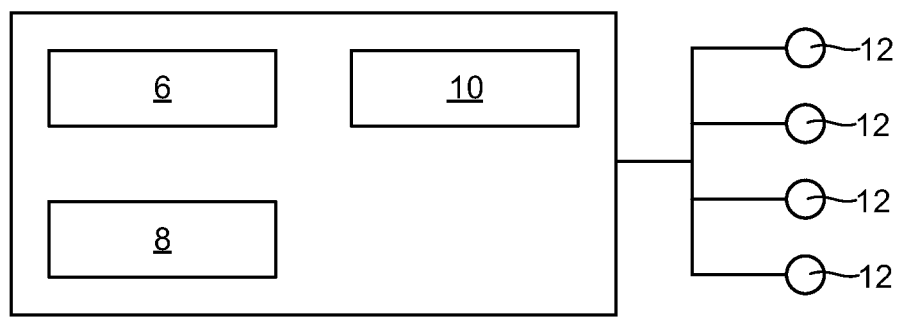

FIG. 1 schematically depicts an apparatus 2 for phase tracking an oscillatory signal according to an embodiment.

The apparatus 2 comprises an input unit 6 that receives an input signal. The input signal may represent measurements of activity in a biological system, such as the human nervous system. The measurements of activity may take any suitable form, including for example any one or more of electrical, chemical, and optical measurements. The measurements of activity may also comprise mechanical measurements, such as using an accelerometer to measure tremor in a limb. In the particular example discussed below, the measurements comprise measurements of electrical activity in the brain obtained using electrodes 12. In embodiments of this type, the electrodes 12 may be implemented using any of various techniques known in the art. In some embodiments, the electrodes 12 are configured to measure a local field potential (LFP). As mentioned above, the LFP is a wide-band recording capturing both action potentials and other membrane potential-derived fluctuations in a small neuronal volume, and can be recording using a macro or microelectrode. In some embodiments, the electrodes 12 are configured to obtain an electrocorticogram (ECoG) recordings from the cortical surface, EEG from the surfaces of scull and EMG from the muscles.

The apparatus 2 further comprises a phase estimation unit 8 that outputs real time estimates of a phase of a target frequency component of the input signal received by the input unit 6. Example implementations of the phase estimation unit 8 will be described in further detail below, with reference to FIG. 2 in particular.

The apparatus further comprises a stimulation unit 10 that generates a stimulation signal for applying phase locked stimulation to the biological system (e.g. brain) based on the estimates of phase provided by the phase estimation unit 8. The measurements of activity in the biological system may not necessarily interact with the same part of the biological system as the stimulation. For example, the measurements of activity may comprise measuring tremor in a limb using accelerometers and the stimulation may be applied to the nervous system.

Figure 2:
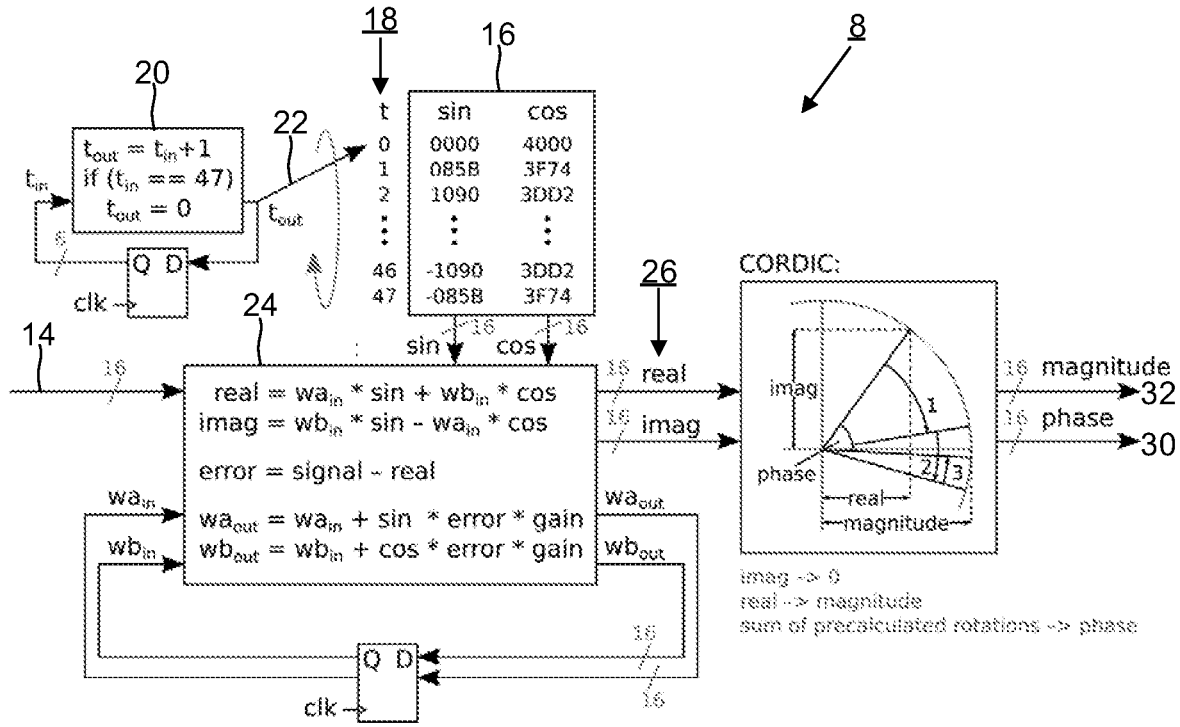

FIG. 2 is a top-level schematic of how the phase estimation unit 8 is realised as a digital circuit according to one class of embodiment.

The phase estimation unit 8 matches an input signal 14 to a weighted sum of a first reference oscillatory signal and a second reference oscillatory signal by iteratively varying weights of the weighted sum. The phase estimation unit 8 generates the first reference oscillatory signal and the second reference oscillatory signal at a frequency corresponding (e.g. equal) to a frequency of a target frequency component in the input signal. Embodiments of the disclosure are particularly advantageous relative to alternative approaches where the frequency of the target frequency component is relatively high, for example greater than 15 Hz, optionally greater than 20 Hz, optionally greater than 25 Hz, optionally greater than 30 Hz. The first and second reference oscillatory signals have the same frequency. In some embodiments, the first and second reference oscillatory signals are both sinusoidal. The first reference oscillatory signal and the second reference oscillatory signal are phase shifted relative to each other. In some embodiments, the first reference oscillatory signal and the second reference oscillatory signal are phase shifted relative to each other by $\pi/2$ radians. In some embodiments, the first reference oscillatory signal and the second reference oscillatory signal are sinusoidal and phase shifted relative to each other by $\pi/2$ radians, taking the forms respectively of a sine curve and a cosine curve.

The weights of the weighted sum and the first and second reference oscillatory signals are used to provide the real time estimates of the phase of the target frequency component.

In the example implementation of FIG. 2, the phase estimation unit 8 is configured to access values of the first reference oscillatory signal and the second reference oscillatory signal from a look-up table 16. The look-up table 16 stores a first reference value for each of a plurality of time points 18. The time points 18 represent a sequence of points in time (e.g. separated in time by a clock cycle, as described below). The variation of the first reference value as a function of time point defines the oscillatory form of the first reference oscillatory signal. In the example shown, the oscillatory form is sinusoidal and an exemplary sequence of first reference values is provided below the word "sin" in the loop-up table 16 of FIG. 2. The look-up table 16 further stores a second reference value for each of the plurality of time points 18. The variation of the second reference value as a function of time point defines the oscillatory form of the second reference oscillatory signal. In the example shown, the oscillatory form is sinusoidal and an exemplary sequence of second reference values is provided below the word "cos" in the look-up table 16 of FIG. 2.

In some embodiments, the phase estimation unit 8 comprises circuitry configured to perform predetermined data processing operations during each of a plurality of clock cycles. A clock signal clk is provided to define the timing of the clock cycles. A different sample of the input signal 14 is processed during each clock cycle. A counter circuit 20 uses the clock signal clk to provide a count signal 22 that cycles through the time points 18 in the look-up table 16, stepping forward one time point for each clock cycle until the last time point is reached (t=47 in the particular example shown) and then returning to the beginning (t=0). Some optimization is possible on this e.g. if the number of points in a cycle is chosen to be devisable by four then with slight modification of the counter only a quarter of a single wave need be stored in the table. This is an example of a class of embodiments in which the look-up table 16 store values associated with time points spanning only a portion of the period of the first reference oscillatory signal and the second reference oscillatory signal (e.g. a quarter of the period), and the phase estimation unit 8 uses symmetry of the first reference oscillatory signal and the second reference oscillatory signal (e.g. the symmetry associated with the sinusoidal form which means that a quarter of the sinusoidal waveform can be used to generate the rest of the sinusoidal waveform using basic mirror symmetry operations) to generate values for time points spanning all of the period of the first reference oscillatory signal and the second reference oscillatory signal based on the values stored in the look-up table 16. In the scheme used angles were represented using 16-bit registers with $2^{-16}$ of a rotation per bit. Amplitudes of the reference waves were $\pm 2^{14}$ allowing them to occupy 16-bit signed registers without overflow. To compensate for this scaling the multipliers used to calculate the product of the reference and the weights (or error) discard the 14 least significant bits (equivalent to dividing by $2^{14}$). Furthermore, if the gain term (discussed below) is chosen as a power of two (e.g. $2^{-5}$) then the gain multiplication can be achieved without active components as it is reduced to further truncation.

For each clock cycle, an adaptive filter block 24 receives a sample of the input signal 14 and a value from each of the first reference oscillatory signal and the second reference oscillatory signal from the look-up table 16. The adaptive filter block 24 matches the input signal 14 to the first reference oscillatory signal and the second reference oscillatory signal by iteratively updating weights in the weighted sum to minimise an error. In the implementation shown, the weights applied to a current sample of the input signal are labelled $wa_{in}$ and $wb_{in}$. An estimate of a real part of the input signal (real) is given as $wa_{in}$ sin t+$wb_{in}$ cos t, where t represents the time point corresponding to the clock signal clk (e.g. in the implementation shown, sin t and cos t represent the outputs of the lookup table 16 which in turn depend on the output 22 from the counter 20 and which in turn changes every clock cycle and represents t). An estimate of an imaginary part of the input signal (imag) is given as $wb_{in}$ sin t−$wa_{in}$ cos t. Weights to be used to process a next sample, $wa_{out}$ and $wb_{out}$, are obtained from the input signal 14 based on a difference (error) between the actual input signal and the estimate of the real part of the input signal (real) provided by the weighted sum (error=signal−real), and a gain term, according to the following expressions: $wa_{out}=wa_{in}+$sin t×error×gain and $wb_{out}=wb_{in}+$cos t×error× gain.

The rate of change of the weights is controlled by the gain term. The output 26 from the adaptive filter block 24 is a band pass filtered version of the input signal 14 with the pass band centred at the frequency of the first and second reference oscillatory signals, while the gain term sets the width of the pass band. The weights and first and second reference oscillatory signals are also used to calculate the imaginary part of the filtered signal and then the angle of the resulting vector is calculated to produce a phase estimate. Thus, the weights of the weighted sum and the first and second reference oscillatory signals are used to provide a real time estimate of the phase of the target frequency component (e.g. sample by sample). In embodiments where this functionality is implemented as a digital circuit this polar to cartesian conversion can be performed using a CORDIC (also known as Volder's algorithm; see Volder, J. E. (1959); The CORDIC Trigonometric Computing Technique; IRE Transactions on Electronic Computers EC-8, 330-334).

The above approach can be generalized to use more than two reference oscillatory signals. The additional reference oscillatory signals may comprise one or more reference oscillatory signals having frequencies equal to one or more respective harmonics of the target frequency component, for example.

The approach of FIG. 2 uses a digital circuit. The methodology could alternatively be implemented on an embedded processor/controller. Depending on the computational resources available, many of the optimisations outlined can still be used, allowing use of low power non-floating-point controllers.

Figure 3:
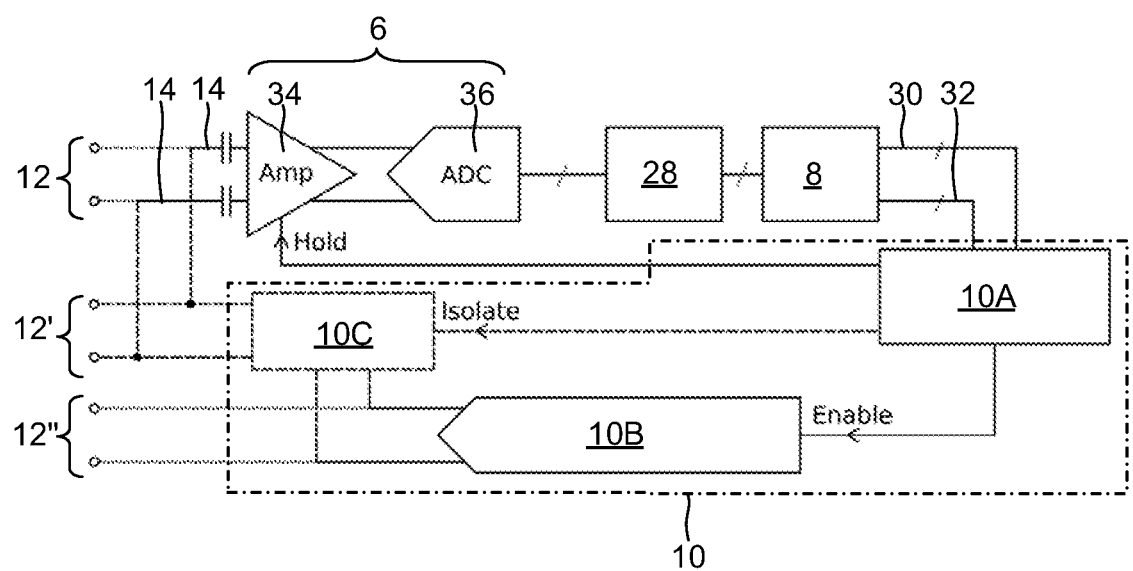
FIG. 3 depicts an example single channel signal chain.

FIG. 3 depicts an example signal chain in which the apparatus 2 for phase tracking oscillatory neuronal signals may operate to provide stimulations that are phase locked to neuronal oscillations (including oscillations that are transient in nature). In the embodiment shown, components corresponding to the input unit 6 of FIG. 1 include an analogue signal conditioning amplifier 34 and an analogue to digital converter 36 configured to receive input signals 14 from electrodes 12 and 12' located at different body locations. In one class of embodiments, combined electrodes 12' are used both as sensors (to provide the input signals 14) and as electrodes to provide stimulation. Connections used for such a combined electrode configuration are depicted by simple dashed lines in FIG. 3. In other embodiments, dedicated input electrodes 12 (for providing the input signals 14) and output electrodes 12" (for providing stimulation) are provided. Connections used for such a dedicated electrode configuration are depicted by dotted lines in FIG. 3.

It is desirable for the signal to be AC coupled to prevent large low frequency drifts from dominating the signal. Typically, such as in the case of electrodes located in deep brain structures (e.g. sub thalamic nucleus) or at the brain surface (electrocorticography/electroencephalography), high gain high input impedance signal conditioning amplifiers are used. It is desirable to include a hold circuit to hold the input at the pre-stimulation potential during stimulation events thus allowing the amplifiers to rapidly settle when acquisition is re-enabled post stimulation. It is desirable that the input signal to the phase estimation unit 8 does not contain a DC offset. Despite AC coupling, these high gain front ends often produce a slight offset and this is desirably removed using a low order high pass digital filter 28.

The phase estimation unit 8 provides real-time estimated phases via phase output 30 and real-time estimated magnitudes via amplitude output 32. The phase output 30 is used to drive a stimulation unit 10. In one class of embodiments, this is implemented by the stimulation unit 10 generating a time-localized stimulation when the estimated phase passes through a predetermined phase threshold $\theta_T$, optionally in a predetermined direction (e.g. in a direction of increasing phase), as depicted schematically in FIGS. 4 and 5 discussed below or optionally, passes into a predetermined phase range (e.g. one sixteenth of a cycle located above $\theta_T$). The time-localized stimulation is time-localized in the sense that a duration of the stimulation is confined to a period that is significantly shorter than a period of the first and second reference oscillatory signals. In the example signal chain depicted in FIG. 3, the stimulation unit 10 comprises a trigger circuit 10A configured to generate a trigger signal when the phase rises through the predetermined phase threshold $\theta_T$. The stimulation unit 10 further comprises a stimulation driver 10B. In an embodiment, the stimulation driver 10B comprises a current source or a voltage source providing electrical stimulation (either through dedicated electrodes 12" or through one or more electrodes 12' that are also used for measuring). In other embodiments, the stimulation driver 10B is configured to drive other mechanisms for providing stimulation, such as a light source (e.g. LED) configured to interact with light sensitive ion channels within tissue.

For combined electrode configurations, the stimulation unit 10 further comprises a stimulation isolator circuit 10C which selectively isolates the measurement branch of the circuit (i.e. the branch containing the phase estimation unit 8) from the stimulation branch of the circuit (i.e. the branch containing the stimulation driver 10B). In the particular implementation shown, the stimulation isolator circuit 10C is controlled by a signal from the trigger circuit 10A.

Figure 4:
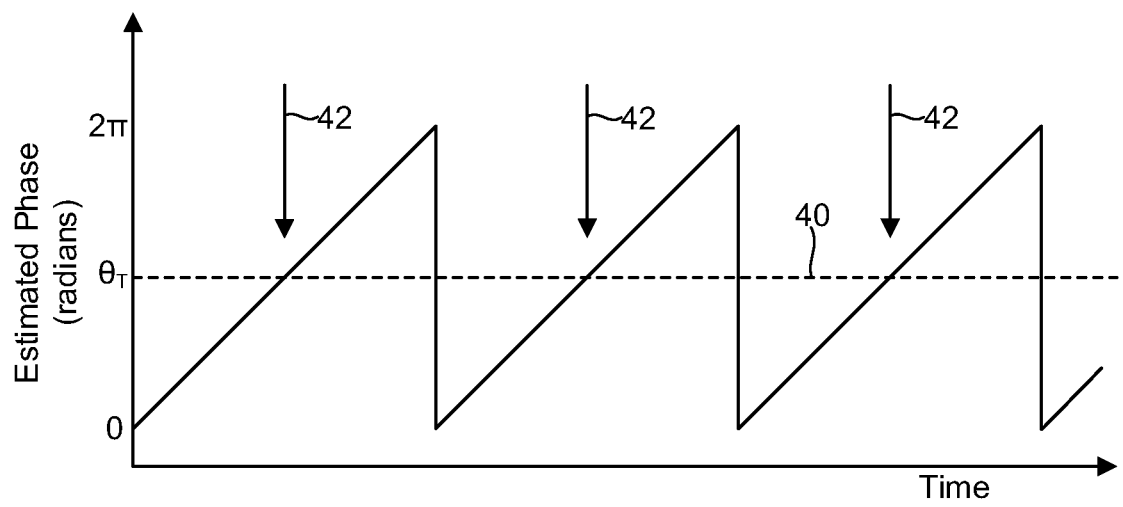
FIG. 4 is graph of estimated phase against time depicting trigger points for generating a time-localized stimulation when an estimated phase passes through a predetermined phase threshold.

FIG. 4 is a graph of estimated phase against time in a case where the estimated phase provided by the phase estimation unit 8 progresses in a stable manner with time. The rate of change of estimated phase is constant, as expected for a sinusoidally varying input signal 14 with constant angular frequency. The saw-tooth form arises by subtracting $2\pi$ radians from the phase at the end of each cycle. The predetermined phase threshold $\theta_T$ corresponds to the level indicated by the horizontal broken line 40. The estimated phase passes the predetermined phase threshold $\theta_T$ at the time points 42 indicated by the arrows. In the example of FIG. 4, time-localized stimulations triggered at each of the time points 42 would be evenly spaced and would occur at the same point in the cycle of the target frequency component for each period of the target frequency component, thereby achieving good phase locking of the stimulation to the target frequency component.

Figure 5:
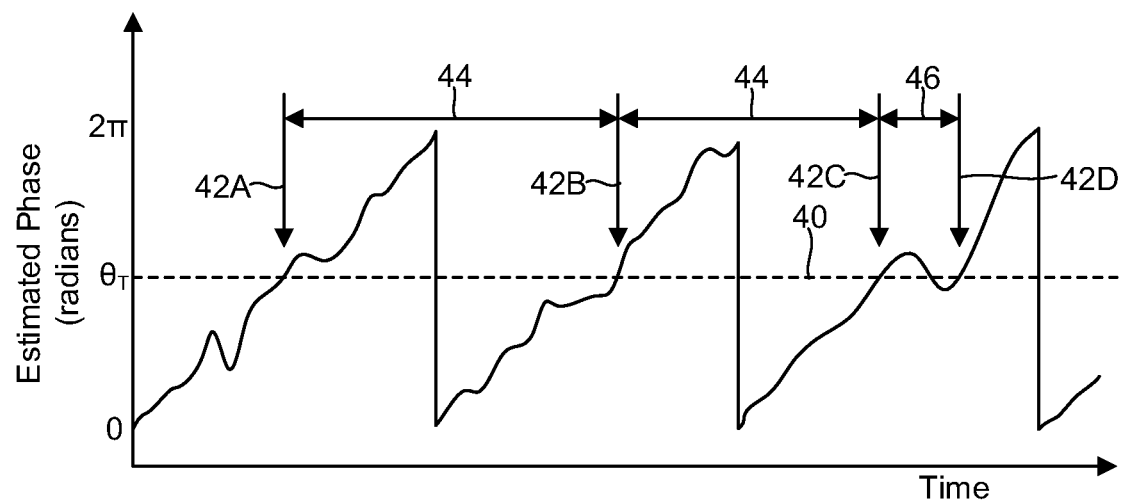
FIG. 5 is graph of the type depicted in FIG. 3 in a case where there is instability in the variation of the estimated phase with time.

In practice, significant fluctuations may occur in the progression of the phase estimate provided by phase estimation unit 8, as depicted schematically in FIG. 5. In order to reduce or prevent erroneous triggering of stimulation by the fluctuations, in some embodiments the stimulation unit 10 suppresses triggering of the time-localized stimulation in a case where the estimated phase passes through the predetermined phase threshold $\theta_T$ or passes into a predetermined phase range within a time period shorter than a predetermined fraction, optionally within 95%, optionally within 90%, optionally within 80%, optionally within 70%, optionally within 60%, of a period of the target frequency component since a preceding passing of the estimated phase through the predetermined phase threshold $\theta_T$ or preceding passing into a predetermined phase range. Thus, while the stimulation unit 10 generates a stimulation signal for triggering a time-localised stimulation to a biological system at each of one or more instances of the estimated phase passing through the predetermined phase threshold $\theta_T$ or into the predetermined phase range, the stimulation signal may be generated in such a way as to suppress the triggering at a subset of the instances selected based on determinations of when the estimated phase passes through the predetermined phase threshold $\theta_T$ or predetermined phase range too early. In the example of FIG. 5, the estimated phase passes through the predetermined phase threshold $\theta_T$ at four time points 42A-42D. The stimulation unit 10 triggers the time-localized stimulation at time points 42A-C but not at time point 42D. At time point 42D, the stimulation unit 10 detects that the estimated phase has passed through the predetermined phase threshold $\theta_T$ (at time point 42D) within the predetermined fraction of the period of the target frequency component since a preceding passing of the estimated phase through the predetermined phase threshold $\theta_T$ (at point 42C). The time period marked 46 between time points 42C and 42D is effectively judged to be too short for it to be appropriate to trigger the stimulation at time point 42D. The stimulation unit 10 thus waits for the next passing of the predetermined phase threshold $\theta_T$. This selective suppression of the stimulation triggering can be implemented for example via an appropriate counter-based circuit within the trigger circuit 10A. The inventors have found by simulation and testing that the selective suppression efficiently ensures that most of the time-localized stimulations occur correctly at the desired phase even in the presence of significant phase fluctuations.

In the scheme depicted in FIG. 2 and described above the property that digital registers naturally wrap around to zero on overflowing the maximum value is exploited to remove the need for the 2π correction per cycle and such registers can be viewed as circular registers. Note also that the sharp falling lines depicted in FIGS. 3 and 4 are the times of this wraparound of the circular registers. In general, embodiments based on clocked systems operating on discrete samples do not contain any sample points in this falling line. Thus if in such embodiments the threshold crossing is triggered by passing into a phase range of interest (e.g. one sixteenth of a cycle located above $\theta_T$) then such wraparound times do not produce a trigger event even in the absence of a directionality requirement. Furthermore, in a digital circuit, testing for such a condition only requires testing for a specific value of the three most significant bits in the case of a phase range of interest equal to one sixteenth of a cycle (two bits for one eight and so on). Alignment of the boundaries of the phase range of interest to allow any arbitrary trigger phase can be achieved by addition of a constant phase shift.

In a variation on the above approach, the same idea of detecting when the estimated phase passes too soon through the predetermined phase threshold $\theta_T$ (or into a predetermined phase range of interest) can be used to provide an output indicative of the accuracy or quality of the phase tracking process. In such an embodiment, the phase estimation unit 8 outputs data representing when the estimated phase passes through a predetermined phase threshold $\theta_T$ or into a predetermined phase range (which may or may not be used to trigger a stimulation) in each of at least a subset of cycles of the target frequency component of the input signal. The phase estimation unit 8 then determines, for each passing of the estimated phase through the predetermined phase threshold $\theta_T$ (or into a predetermined phase range), whether the estimated phase has passed through the predetermined phase threshold $\theta_T$ (or into a predetermined phase range) within a time period shorter than a predetermined fraction of a period of the target frequency component since a preceding passing of the estimated phase through the predetermined phase threshold $\theta_T$ (or into a predetermined phase range). The phase estimation unit 8 then outputs data representing a result of the determination. The data thus output may form the basis of a Boolean phase quality estimate for a phase of interest. If there has been an earlier phase crossing too soon the phase estimate is deemed low quality, otherwise the phase estimate is deemed high quality. The generation of the phase quality estimate in this manner is not restricted to cases where the phase estimation is achieved using the particular phase estimation methods described above with reference to FIGS. 1 to 5, but may be applied more generally.

The high level of suppression of target frequency components that is made possible by embodiments of the disclosure opens up the possibility for reducing the amount of stimulation that is applied. For example, when an effect state is maintained in which a target frequency component has been sufficiently suppressed, the target frequency component may remain suppressed for a period of time after a most recent stimulation even if stimulation is temporarily stopped. In some embodiments, such time periods are detected and used to reduce or temporarily remove stimulation. In the embodiment discussed above where instances of the estimated phase passing through the predetermined phase threshold $\theta_T$ or into the predetermined phase range are detected, triggering may be suppressed at a selected subset of the instances. In some embodiments, triggering is suppressed at one or more non-standard instances. Non-standard instances are instances where the triggering would otherwise occur too early. Each non-standard instance corresponds to where the estimated phase has been determined to have passed through the predetermined phase threshold $\theta_T$ or into the predetermined phase range within a time period shorter than the predetermined fraction of the period of the target frequency component since the preceding passing of the estimated phase through the predetermined phase threshold $\theta_T$ or into the predetermined phase range. However, the instances may be selected to additionally or alternatively suppress the triggering at one or more standard instances. Standard instances are instances where the triggering would otherwise have occurred at the expected time (e.g. once per cycle of the target frequency component). Standard instances may thus correspond to where the estimated phase has been determined not to have passed through the predetermined phase threshold $\theta_T$ or into the predetermined phase range within a time period shorter than the predetermined fraction of the period of the target frequency component since the preceding passing of the estimated phase through the predetermined phase threshold $\theta_T$ or into the predetermined phase range. Suppressing triggering at standard instances may be desirable in situations where it has been determined, or it is expected, that the stimulation has caused temporary suppression of the target frequency component to a satisfactory level, so that the need for stimulation during this time period is reduced or removed. In an embodiment, the instances are selected to suppress a selected proportion of standard instances occurring in a time window; and the selected proportion is selected based on an expected frequency of occurrence of the non-standard instances in the time window (e.g. by determining a frequency of occurrence of the non-standard instances in a recent, for example directly preceding, time window). For example, triggering may be suppressed at every $2^{nd}$, $3^{rd}$, $4^{th}$, etc., standard instance (or any appropriate rule that provides a suitable level of triggering). A relatively high frequency of non-standard instances may be a signature of a high level of suppression of the target frequency component and therefore acts as a convenient and reliable metric by which to measure such a state. In an embodiment, the selected proportion is selected based on a ratio of the number of non-standard instances to the number of standard instances in a preceding time window. Higher levels of this ratio may indicate higher levels of suppression of the target frequency component (where stimulation should be suspended) and lower levels of the ratio may indicate lower levels of suppression (where stimulation should be applied). In other embodiments, the apparatus may be configured to measure a power of the target frequency component and use the measured power to vary the amount of stimulation. For example, the apparatus may be configured to modify the stimulation signal to selectively reduce the stimulation (e.g. suppress triggering of stimulation) when the measured power of the target frequency component falls below a predetermined threshold.

In some embodiments, instead of generating time-localized stimulations based on the estimated phases, the stimulation unit 10 may be configured to modulate a continuous stimulation signal based on the estimated phases, for example using a look-up table or similar. For continuous stimulation it is more difficult to halt stimulation if the phase estimate is fluctuating away from the expected rate of phase progression and hence this type of stimulation is more suited to cases where the oscillation is more continuous and stable. Despite this, steps can be taken to account for fluctuations. Depending on the requirements of the stimulation pattern (implemented in the lookup table), it can also be useful to include a rate of change phase estimate detection calculation (subtraction with smoothing filter e.g. running average). Deviations outside the desired range can then be used to switch the look up to a set of alternative values in the lookup table. The rate of phase change signal can also be used to smooth the phase estimate. It should be noted however that smoothing/filtering reduces responsiveness. Additionally, a threshold on the magnitude signal can be used to prevent stimulation at times of low input signal amplitude. If used for this purpose it is often useful to smooth the amplitude signal.

Multiple input channels allow flexibility to select the signals of interest from a pool of inputs and adapt to the requirements of the biological or other real world system being manipulated. Often the ability to measure the signal between two areas is required. A slightly more complex version of this is to track the differential between the average of one group of signals and the average of another group of signals and to be able to switch signals in and out of each group. This can be achieved by adding multiplexors to the analogue input stages which implement digitally controlled time division multiplexing to sequentially provide samples to the analogue to digital converter. The resulting digital stream at the output of the converter 36 can be selectively multiplexed to feed a serial adder with subtract enable which in turn feeds a phase estimation unit 8. This allows the input to the phase estimation unit 8 to be a selective sum or difference of the raw input signals, thus facilitating dynamic re-referencing. A separate multi-channel functionality is to be able to not only track the phase of a differential (re-referenced) input but the difference between the individually calculated phases of two inputs. Two serial adders placed in parallel feeding independent phase calculations and subtraction of the outputs achieves this. Note, the phase estimation unit 8 need not be fully duplicated if it processes the values sequentially. Also, in such a situation the phase output is no longer expected to be steadily progressing so the phase quality estimates as described above would need to be applied before the final subtraction and trigger requirements would be different and application specific.

Embodiments described above implement the phase estimation unit 8 with a fixed centre tuning frequency (i.e. the frequency of the first and second reference oscillatory signals is constant). However, biological oscillations and other real world signals often slightly vary around a mean frequency over time. As described already, the gain term in the phase estimation unit 8 sets the width around the centre frequency of the effective pass band filter in the phase estimation unit 8. This allows a certain flexibility in providing specificity to a frequency of interest yet creates a system with adaptability to capture frequency variations in the signal. There is an inherent trade-off in this and if the signal varies such that it requires a large width setting it can result in insufficient specificity for the signal's actual frequency at any given time.

In some embodiments, the apparatus 2 adaptively controls the frequency of the first and second reference oscillatory components (thereby effectively adapting the centre tuning frequency of the phase estimation unit 8). In embodiments of the type described above with reference to FIG. 2, the frequency of the first and second reference oscillatory components is the sample rate (defined by the clock cycle) divided by the number of time points in the look-up table 16. Either or both of the sample rate and the number of time points in the look-up table 16 can be manipulated to provide the desired frequency control. Thus, in some embodiments the adaptive control is implemented by changing the duration of the clock cycle. Decreasing the clock cycle increases the tuning frequency and increasing the clock cycle decreases the tuning frequency. The apparatus 2 may thus comprise a tuning circuit that varies the clock frequency and thus the clock cycle (or sampling rate). Alternatively or additionally, the phase estimation unit 8 comprises a plurality of look-up tables. Each look-up table has a different number of time points. The adaptive control is implemented by selectively switching between different ones of the look-up tables. If there are multiple look-up tables, it may be particularly desirable to make use of symmetries in the first and second reference oscillatory signals to keep the number of time points in the look-up table to a minimum, as described above. In some embodiments, the apparatus 2 has look-up tables having one or more of the following numbers of time points: 40, 44, 48 and so on up to 68 and 72 time points, which due to symmetry amounts to a total 116 values in the table. For a clock frequency (sampling rate) of 1 kHz this would accommodate centre frequencies of 25, 22.7, 20.8 and so on down to 14.7 and 13.9 Hz. This provides sufficient resolution to switch the tuning frequency within a range of interest. Additionally, if a fully flexible system is required the entire range can be shifted by adding the functionality to switch through a number of sample rates. For example, 0.5, 1, 2, 4, 8, 16, 32 kHz and a lookup table with number of time points ranging from 40 to 72 supports centre frequencies from 6.9 Hz up to 800 Hz. Note, even higher centre frequencies can be achieved with higher sample rates or reduced time points per cycle.

The various programmable options outlined above can be set through a bank of configuration registers. When multiplexors are present control logic and state machines can be included to allow the multiplexors to automatically cycle through the enabled channels and implement the averaging and differential signalling mentioned as well as the time division multiplexing schemes described. Additionally, in many applications which would benefit from adaptive tuning of these parameters the system can include a microcontroller or digital processor running parameter tuning algorithms specific to the application. The controller/processor can power up intermittently (or run continuously) to monitor the outputs of the system and based on the readouts tune the configuration values (i.e. write to the configuration registers). This provides a means for the system to ensure it is always appropriately tracking—and potentially appropriately stimulating based on—the signal of interest within the parameter space of interest.

Figure 6:
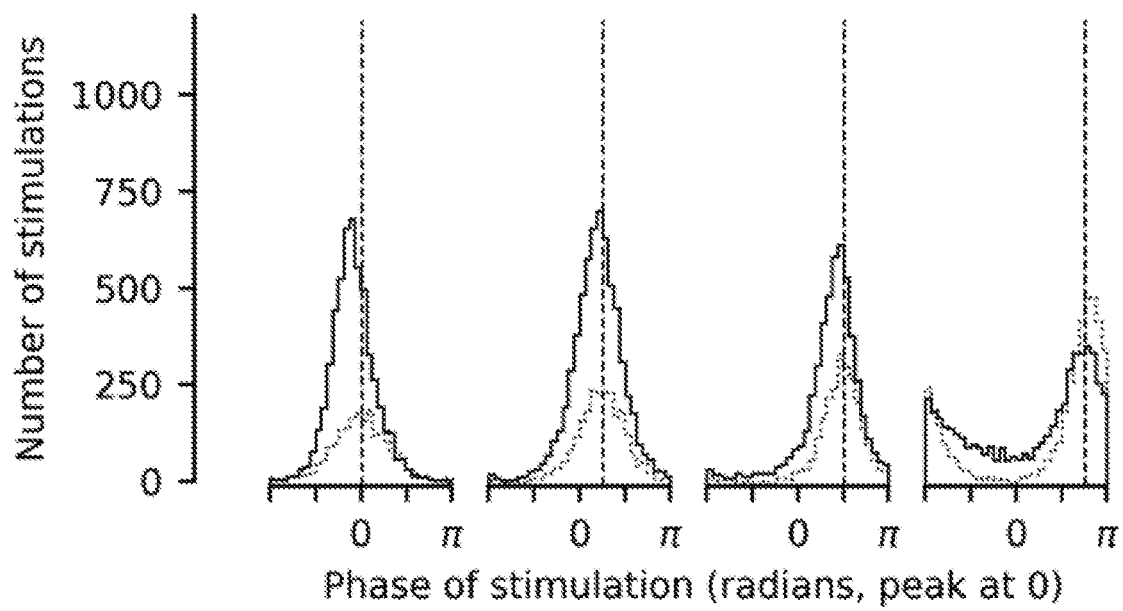
FIGS. 6-9 depict performance of an example apparatus for phase tracking an oscillatory signal when used to provide phase locked stimulations.
Figure 7:
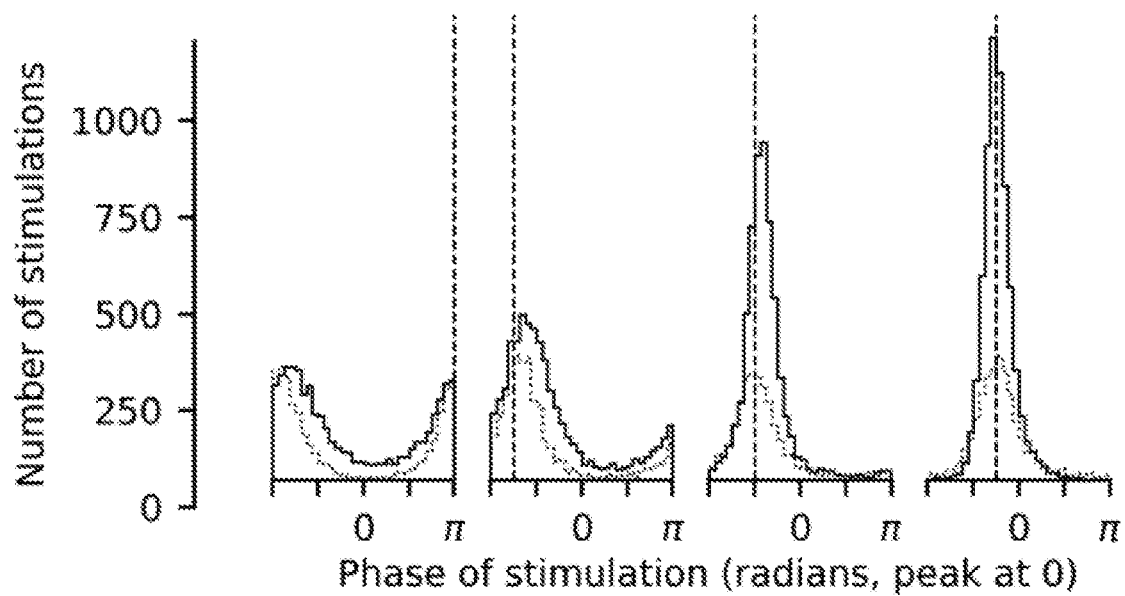
Figure 8:
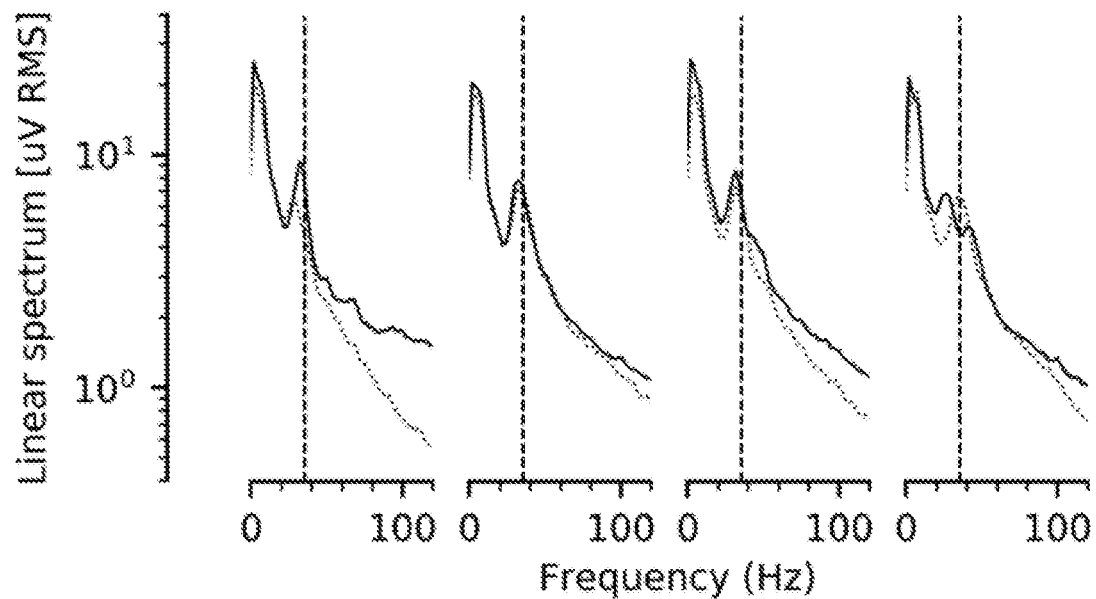
Figure 9:
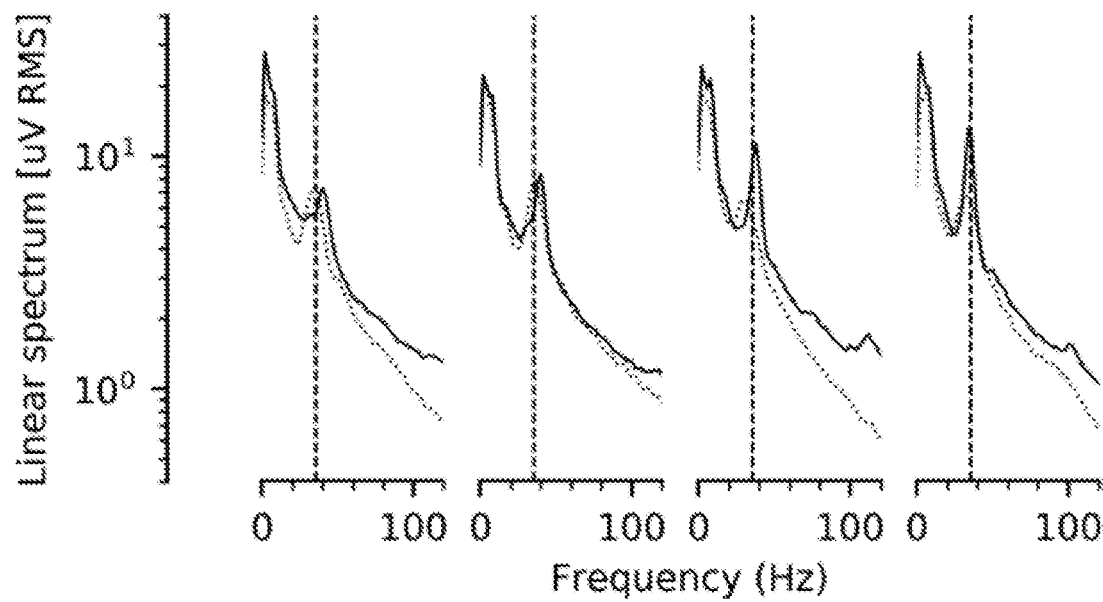

FIGS. 6-9 depict performance of embodiments of the apparatus 2 in the form of recordings of the apparatus 2 providing a burst of three 50 uA 100 ms biphasic charged balanced stimulation pulses in vivo in a Parkinson's disease model rat brain through a pair of stainless-steel electrodes at a predetermined phase of field potentials from a frontal ECoG screw. FIGS. 6 and 7 are histograms depicting online stimulation accuracy by binning stimulation pulses using the offline calculated phase (the offline phase was calculated using a band pass filter followed by Hilbert transform and hence benefited from the future evolution of the signal which was unavailable to the online system). The target phase for the online system is depicted by the vertical dotted lines and each of the panels depicts one of eight target phases spread evenly throughout the cycle. The solid histograms are when stimulation was enabled, and the dotted histograms show the phase of triggers produced by the online system when actual stimulation was disabled (stimulation off condition). Note recording duration of the stimulation off condition was shorter hence less area under the histogram. FIGS. 8 and 9 show corresponding linear spectra with vertical dotted lines showing the target frequency. The suppression of generation of time-localized stimulation in cases where the estimated phase passes into the predetermined phase range within a time period shorter than a predetermined fraction of a period of the target frequency component since a preceding passing of the estimated phase into the predetermined phase range was in effect for these recordings. Note the target phase dependent differences between the histograms and spectra that is present when stimulation is enabled compared to the well matching traces for the stimulation off condition.

Figure 10:
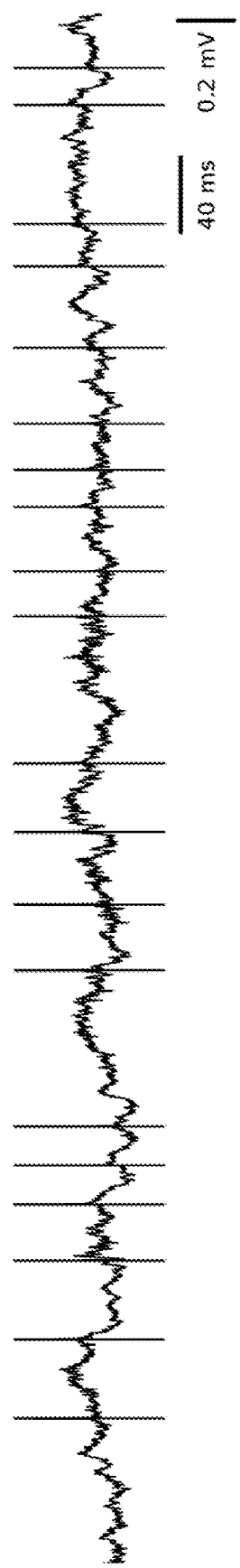
FIGS. 10 and 11 depict example raw recording traces where stimulation was delivered to the globus pallidus, with stimulation respectively targeting the suppressing phase and the amplifying phase.
Figure 11:
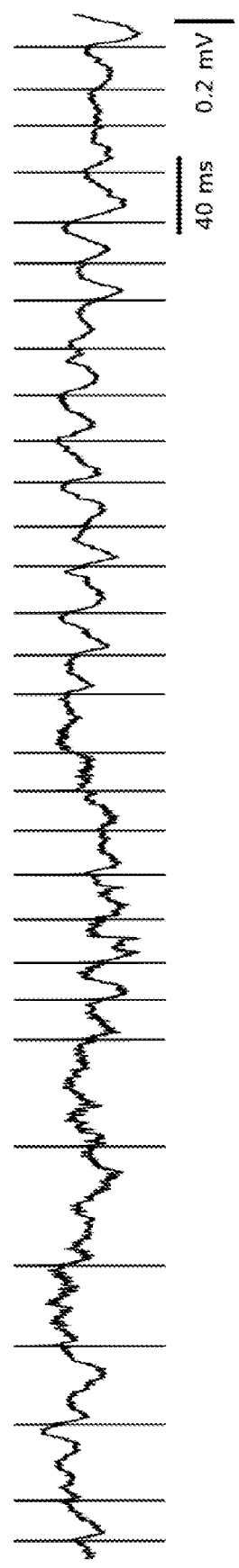

FIGS. 10 and 11 depict example raw recording traces from a similar preparation where stimulation was delivered to the globus pallidus. The sharp electrical artefacts produced by the stimulation are truncated in these figures. In FIG. 10 the predetermined target phase was set to the middle of the ascending phase and the predetermined target frequency was set to 35 Hz producing suppression of the parkinsonian 35 Hz oscillation. In FIG. 11 the predetermined target phase was one eighth of a cycle after the peak producing amplification of the parkinsonian oscillation. The oscillation cycles visible in FIG. 11 are much less evident in FIG. 10, as the system is successfully supressing the oscillation. Note that to successfully achieve and maintain suppression of the target oscillation, the system is stimulating less overall due to the previously outlined rule governing the suppression of generation of time-localized stimulation dependent on time since the previous passing into the predetermined phase range.

Figure 12:
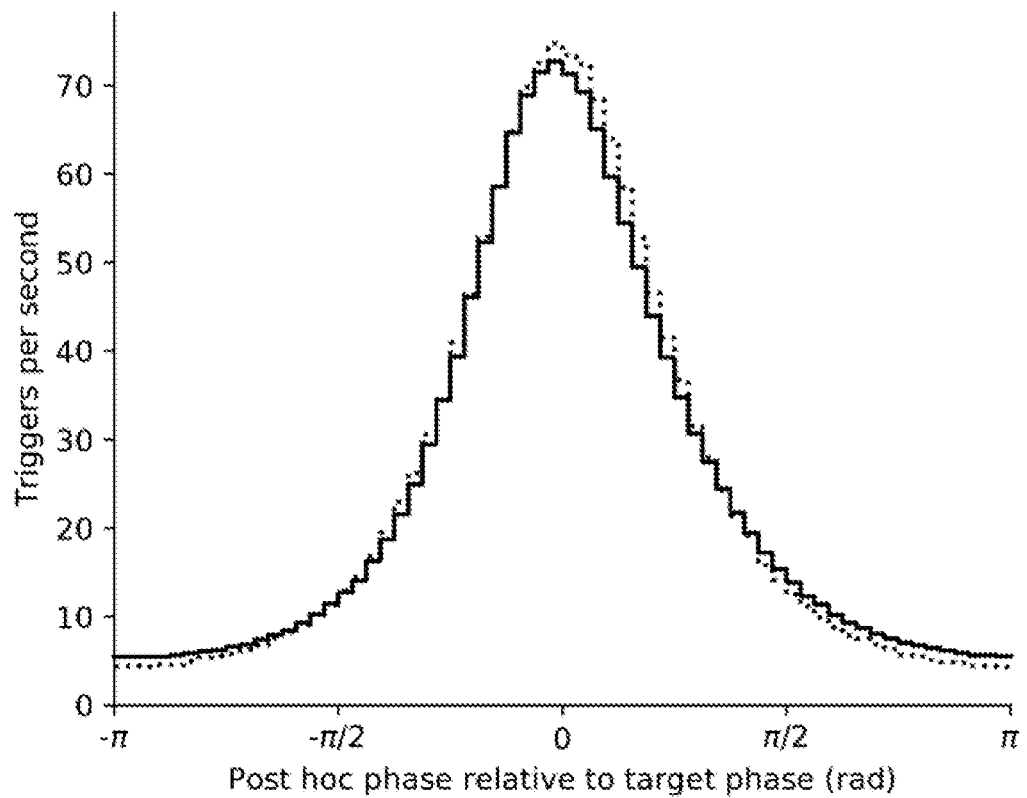
FIG. 12 depicts a group phase histogram showing online stimulation accuracy by binning stimulation pulses using the offline post hoc calculated phase.

FIGS. 12-17 depict mean group data from 7 rats using a similar preparation where stimulation was delivered to the globus pallidus. FIG. 12 depicts the group phase histogram showing online stimulation accuracy by binning stimulation pulses using the offline post hoc calculated phase. The offline phase was calculated using a band pass filter followed by Hilbert transform and hence benefited from the future evolution of the signal, which is unavailable to a real-time system as it is yet to occur at stimulation time. Most stimulation occurs within a quarter cycle of the target phase. The dotted line represents the case of running the system online but without providing actual stimulation and the solid line depicts the phase detection when stimulation was applied. The fact that they are almost identical demonstrates that the system was able to produce full accuracy in the presence of the artefacts produced by the electrical stimulation.

Figure 13:
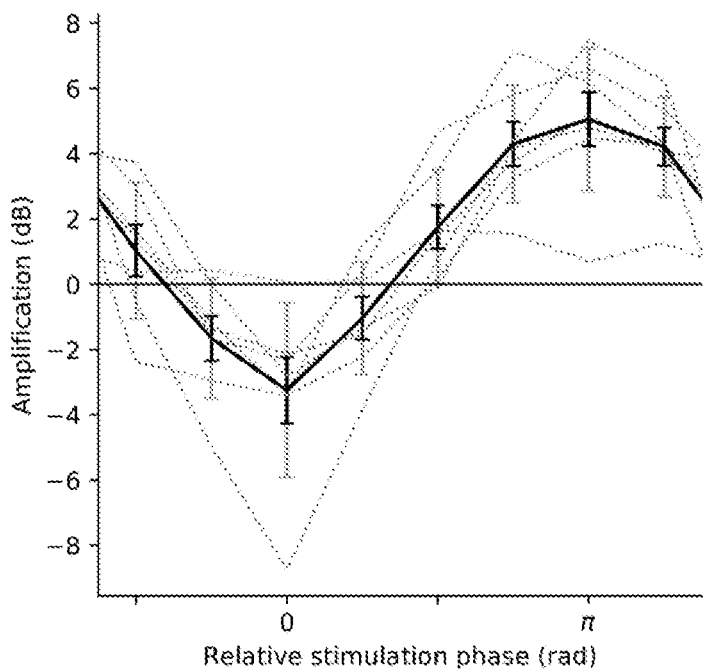
FIG. 13 depicts the amount of amplification/suppression in decibels depending on the target phase of the stimulation relative to the phase that produced the most suppression in that rat.
Figure 14:
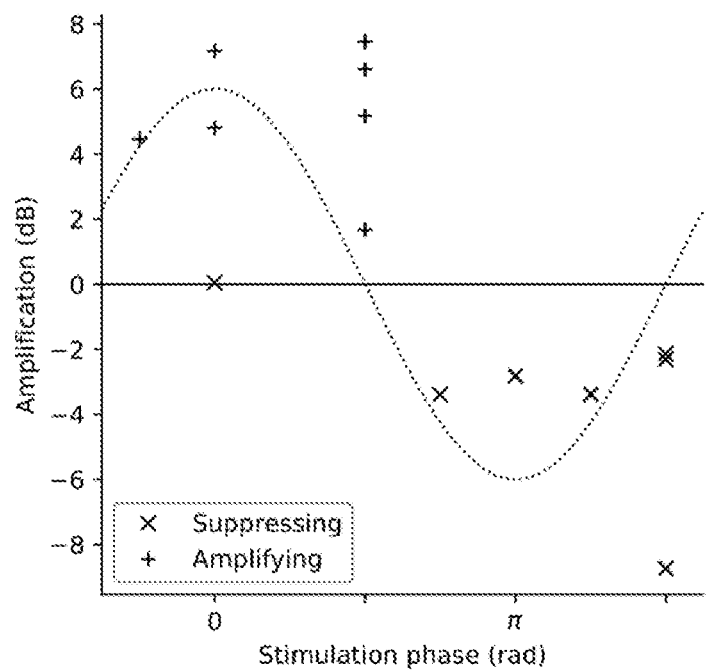
FIG. 14 depicts the absolute target stimulation phase vs amplification/suppression seen in each rat for the most amplifying phase and the most suppressing phase.
Figure 15:
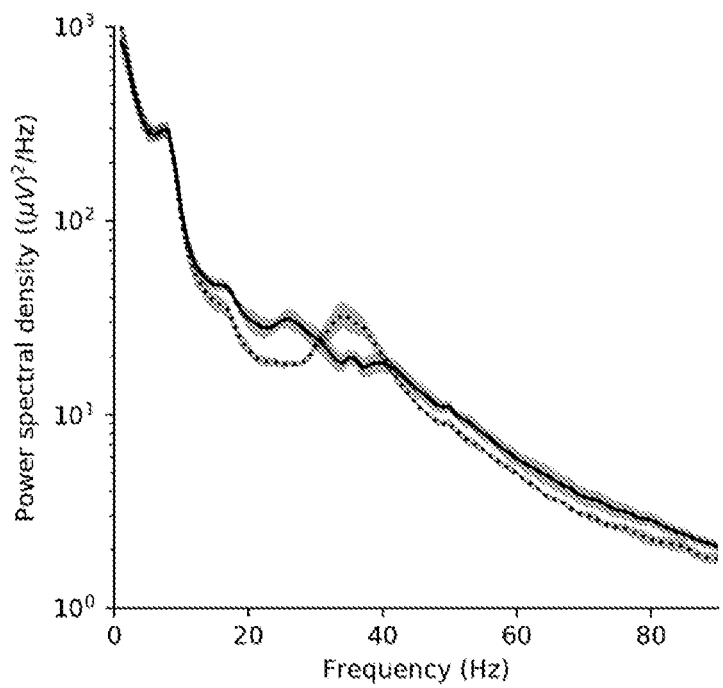
FIGS. 15 and 16 depict power spectra (geometric mean +/−geometric standard error) corresponding respectively to stimulation targeting the suppressing phase and the amplifying phase.
Figure 16:
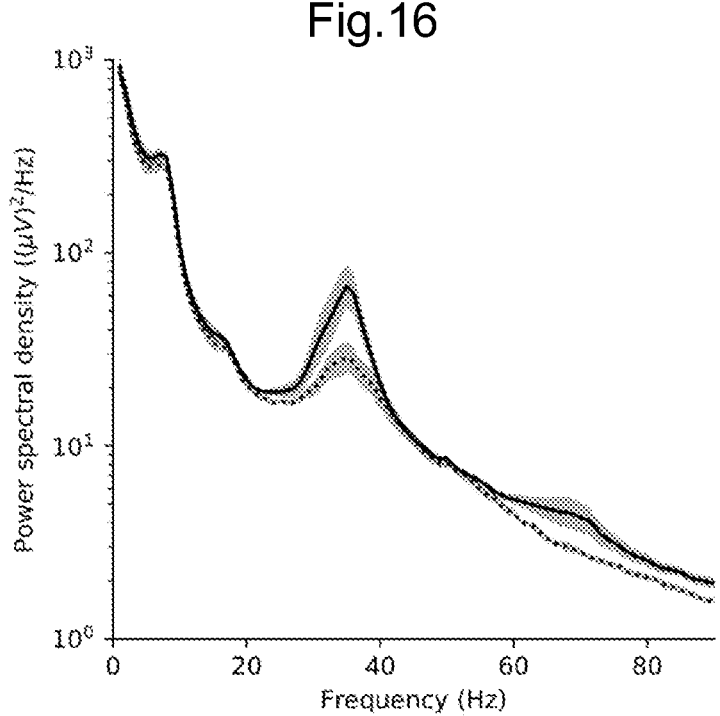

FIG. 13 depicts the amount of amplification/suppression in decibels depending on the target phase of the stimulation relative to the phase that produced the most suppression in that rat. Amplification/suppression was calculated by comparing the signal power measured in the stimulation condition against the no stimulation condition in the 10 Hz around the target frequency. Solid black is group mean across rats+/−standard error of the mean, grey is +/−standard deviation of the mean and the dotted lines represent the trace calculated for each rat. FIG. 14 depicts the absolute target stimulation phase vs amplification/suppression seen in each rat for the most amplifying phase and the most suppressing phase. The dotted trace represents the cycle of the target oscillation. FIGS. 15 and 16 depict the power spectra (geometric mean+/−geometric standard error). The dotted lines are generated from times without stimulation enabled. Note the spectral peak at about 35 Hz representing the parkinsonian 35 Hz oscillation occurring in these dopamine-lesioned rats. The solid line in FIG. 15 is the spectra from times when targeting stimulation to the supressing phase of each rat and the solid line in FIG. 16 is the spectra from times when targeting stimulation to the amplifying phase for each rat. Note the suppression of the spectral peak in FIG. 15 and the amplification of the spectral peak in FIG. 16.

Figure 17:
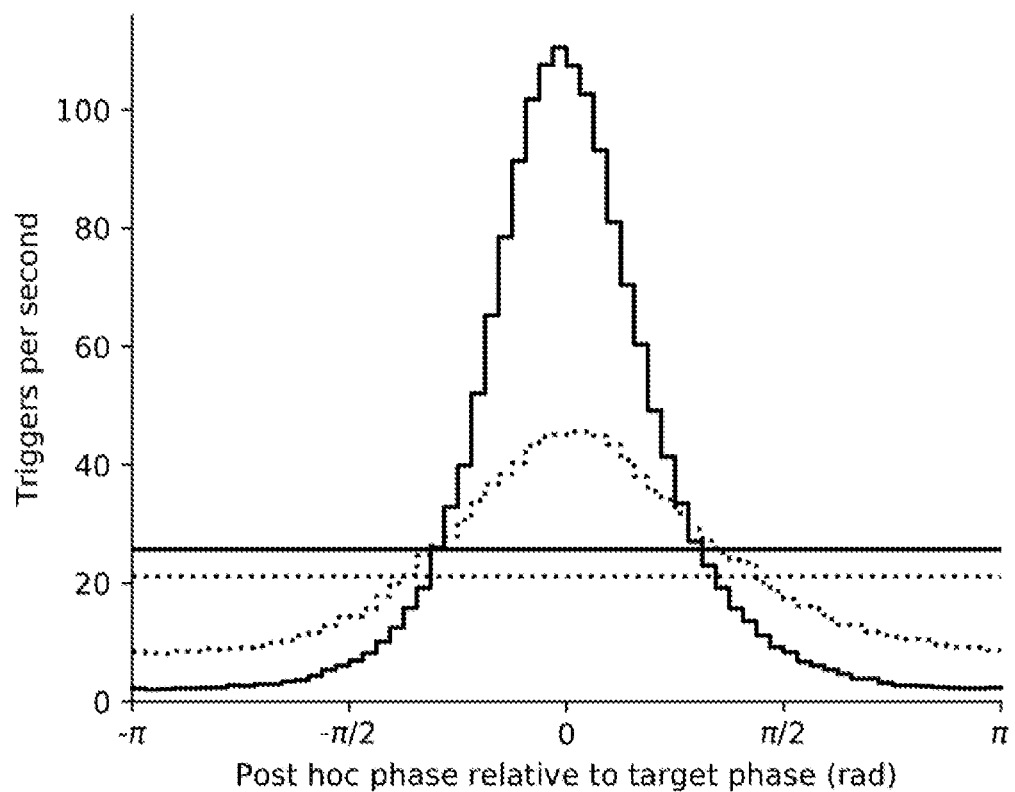
FIG. 17 depicts the mean online vs offline post hoc phase for the suppressing phase (dotted trace) and the amplifying phase (solid trace) of each rat.

FIG. 17 depicts the mean online vs offline post hoc phase for the supressing phase (dotted trace) and the amplifying phase (solid trace) of each rat. Note when amplifying the oscillation the phase information becomes more reliable and when supressing the oscillation the phase information becomes less reliable. The horizontal lines represent the mean stimulation rate, independent of post hoc phase. Note the difference in mean stimulation rate is due to the previously described rule governing the suppression of generation of time-localized stimulation dependent on time since the previous passing into the predetermined phase range.

The invention claimed is:

1. An apparatus for phase tracking an oscillatory signal, comprising:
    an input unit configured to receive an input signal; and
    a phase estimation unit,
    wherein the phase estimation unit is configured to:
    generate first and second reference oscillatory signals at the frequency of a target frequency component of the input signal, the first and second reference oscillatory signals being phase shifted relative to each other;
    iteratively vary weights of a weighted sum of the first and second reference oscillatory signals to match the weighted sum to the input signal; and
    use the weights of the matched weighted sum to provide real time estimates of the phase of the target frequency component of the input signal.

2. The apparatus of claim 1, wherein the input signal represents measurements of activity in a biological system.

3. The apparatus of claim 2, further comprising a stimulation unit configured to generate a stimulation signal for applying phase locked stimulation to the biological system based on the estimates of phase provided by the phase estimation unit.

4. The apparatus of claim 3, wherein the stimulation unit is configured to trigger a time-localised stimulation in response to the estimated phase passing through a predetermined phase threshold or into a predetermined phase range.

5. The apparatus of claim 4, wherein the stimulation unit is configured to suppress triggering of the time-localized stimulation in a case where the estimated phase passes through the predetermined phase threshold or into the predetermined phase range within a time period shorter than a predetermined fraction of a period of the target frequency component since a preceding passing of the estimated phase through the predetermined phase threshold or into the predetermined phase range.

6. The apparatus of claim 1, wherein the phase estimation unit is configured to access values of the first reference oscillatory signal and the second reference oscillatory signal from a look-up table,
    wherein the look-up table stores:
    a first reference value for each of a plurality of time points representing a sequence of points in time, the variation of first reference value as a function of time point defining the oscillatory form of the first reference oscillatory signal; and
    a second reference value for each of the plurality of time points, the variation of second reference value as a function of time point defining the oscillatory form of the second reference oscillatory signal.

7. The apparatus of claim 1, wherein:
the phase estimation unit comprises circuitry configured to perform predetermined data processing operations during each of a plurality of clock cycles;
a different sample of the input signal is processed during each clock cycle; and
the phase estimation unit is configured to cycle through the time points in the look-up table, stepping forward one time point for each clock cycle of the apparatus.

8. The apparatus of claim 7, wherein:
the look-up table stores values associated with time points spanning only a portion of the period of the first reference oscillatory signal and the second reference oscillatory signal; and
the phase estimation unit is configured to use symmetry of the first reference oscillatory signal and the second reference oscillatory signal to generate values for time points spanning all of the period of the first reference oscillatory signal and the second reference oscillatory signal based on the values stored in the look-up table.

9. The apparatus of claim 7, wherein the apparatus is configured to adaptively control the frequency of the first and second reference oscillatory components by changing the duration of the clock cycle.

10. The apparatus of claim 9, wherein:
the phase estimation unit comprises a plurality of the look-up tables, each look-up table having a different number of time points; and
the adaptive control is implemented by selectively switching between different ones of the look-up tables.

11. The apparatus of claim 1, wherein the iterative varying of the weights of the weighted sum is performed using a gain term to control the rate of change of the weights during the iteration.

12. The apparatus of claim 1, wherein:
the phase estimation unit is configured to output data representing when the estimated phase passes through a predetermined phase threshold or into a predetermined phase range in each of at least a subset of cycles of the target frequency component of the input signal; and
the phase estimation unit is further configured to:
determine, for each passing of the estimated phase through the predetermined phase threshold or into the predetermined phase range, whether the estimated phase has passed through the predetermined phase threshold or into the predetermined phase range within a time period shorter than a predetermined fraction of a period of the target frequency component since a preceding passing of the estimated phase through the predetermined phase threshold or into the predetermined phase range; and
output data representing a result of the determination.

13. The apparatus of claim 1, wherein:
the apparatus comprises a stimulation unit configured to generate a stimulation signal for applying phase locked stimulation to the biological system based on the estimates of phase provided by the phase estimation unit;
the apparatus is configured to measure a power of the target frequency component; and
the apparatus is configured to modify the stimulation signal to selectively reduce the stimulation when the measured power of the target frequency component falls below a predetermined threshold.

14. The apparatus of claim 1, wherein the input signal represents measurements of electrical activity in a nervous system of a biological system.

15. An apparatus for phase tracking an oscillatory signal, comprising:
an input unit configured to receive an input signal; and
a phase estimation unit configured to output data representing when an estimated phase of a target frequency component of the input signal passes through a predetermined phase threshold or into a predetermined phase range in each of at least a subset of cycles of the target frequency component of the input signal, wherein:
the phase estimation unit is further configured to:
determine, for each passing of the estimated phase through the predetermined phase threshold or into the predetermined phase range, whether the estimated phase has passed through the predetermined phase threshold or into the predetermined phase range within a time period shorter than a predetermined fraction of a period of the target frequency component since a preceding passing of the estimated phase through the predetermined phase threshold or into the predetermined phase range; and
output data representing a result of the determination.

16. The apparatus of claim 15, wherein:
the apparatus comprises a stimulation unit configured to generate a stimulation signal for triggering a time-localised stimulation to a biological system at each of one or more instances of the estimated phase passing through the predetermined phase threshold or into the predetermined phase range; and
the stimulation signal is generated in such a way as to suppress the triggering at a selected subset of the instances, the selection being based on the output data representing the result of the determination.

17. The apparatus of claim 16, wherein the instances are selected to suppress the triggering at one or more non-standard instances, each non-standard instance corresponding to where the estimated phase has been determined to have passed through the predetermined phase threshold or into the predetermined phase range within a time period shorter than the predetermined fraction of the period of the target frequency component since the preceding passing of the estimated phase through the predetermined phase threshold or into the predetermined phase range.

18. The apparatus of claim 16, wherein:
the instances are selected to suppress the triggering at one or more standard instances corresponding to where the estimated phase has been determined not to have passed through the predetermined phase threshold or into the predetermined phase range within a time period shorter than the predetermined fraction of the period of the target frequency component since the preceding passing of the estimated phase through the predetermined phase threshold or into the predetermined phase range;
the triggering is suppressed at a selected proportion of standard instances occurring in a time window; and
the selected proportion is selected based on an expected frequency of occurrence of the non-standard instances in the time window.

19. The apparatus of claim 18, wherein the selected proportion is selected based on a ratio of the number of non-standard instances to the number of standard instances in a preceding time window.

20. The apparatus of claim 15, wherein the input signal represents measurements of electrical activity in a nervous system of a biological system.

21. A method of phase tracking an oscillatory signal, comprising:
receiving an input signal;
generating first and second reference oscillatory signals at the frequency of a target frequency component of the input signal, the first and second reference oscillatory signals being phase shifted relative to each other;
iteratively varying weights of a weighted sum of the first and second reference oscillatory signals to match the weighted sum to the input signal; and
using the weights of the matched weighted sum to provide real time estimates of the phase of the target frequency component of the input signal.

22. A method of phase tracking an oscillatory signal, comprising:
receiving an input signal;
determining when an estimated phase of a target frequency component of the input signal passes through a predetermined phase threshold or into a predetermined phase range in each of at least a subset of cycles of the target frequency component of the input signal; and
determining, for each passing of the estimated phase through the predetermined phase threshold or into the predetermined phase range, whether the estimated phase has passed through the predetermined phase threshold or into the predetermined phase range within a time period shorter than a predetermined fraction of a period of the target frequency component since a preceding passing of the estimated phase through the predetermined phase threshold or into the predetermined phase range; and
outputting data representing a result of the determination.

* * * * *